United States Patent [19]

Dickhudt

[11] Patent Number: 4,519,403
[45] Date of Patent: May 28, 1985

[54] BALLOON LEAD AND INFLATOR

[75] Inventor: Eugene A. Dickhudt, New Brighton, Minn.

[73] Assignee: Medtronic, Inc., Minneapolis, Minn.

[21] Appl. No.: 489,882

[22] Filed: Apr. 29, 1983

[51] Int. Cl.³ ............................................. A61N 1/04
[52] U.S. Cl. .................................... 128/785; 128/786
[58] Field of Search ............................... 128/784–786, 128/642, 419 P, 675, 748; 604/97, 98, 103

[56] References Cited

U.S. PATENT DOCUMENTS

| | | | |
|---|---|---|---|
| 3,326,207 | 6/1967 | Egan | 128/2.06 |
| 3,448,739 | 6/1969 | Stark et al. | 128/2.05 |
| 3,635,223 | 1/1972 | Klieman | 128/348 |
| 3,837,347 | 9/1974 | Tower | 128/404 |
| 3,937,225 | 2/1976 | Schramm | 128/418 |
| 4,109,654 | 8/1978 | Bolduc et al. | 604/97 |
| 4,141,365 | 2/1979 | Fischell et al. | 128/419 R |
| 4,198,963 | 4/1980 | Barkalow et al. | 128/53 |
| 4,285,347 | 8/1981 | Hess | 128/785 |
| 4,295,464 | 10/1981 | Shihata | 604/98 |
| 4,311,133 | 1/1982 | Robinson | 128/1 D |

FOREIGN PATENT DOCUMENTS 906516  2/1979  U.S.S.R. .............................. 128/642

OTHER PUBLICATIONS

"Siemens–Elema, The 'S' Generation Pacing Leads, Adapters, and Accessories", p. 6, Sep., 1979.
Medtronic Neuro advertisement entitled "Pisces–Sigma Lead, A Proven Performer", ©1983 Medtronic, Inc.

Primary Examiner—Lee S. Cohen
Attorney, Agent, or Firm—Robert J. Klepinski; Joseph F. Breimayer; John L. Rooney

[57] ABSTRACT

A lead for implantation in the epidural space has an inflatable balloon which is sealed against a first side of the lead so it inflates away from the first side. The balloon contacts walls of the epidural space and urges an electrode on the first side against the dura. A syringe for inflating the balloon has a spring to absorb travel of a plunger actuator when fluid pressure in the balloon exceeds tension of the spring.

8 Claims, 4 Drawing Figures

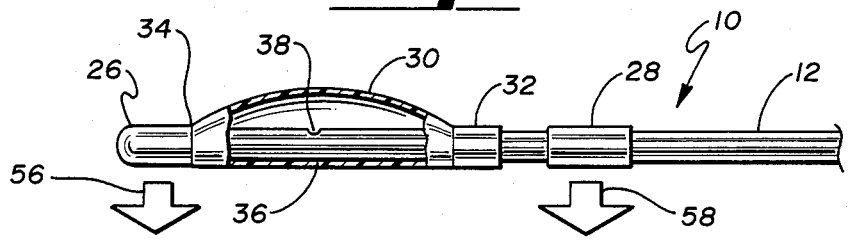
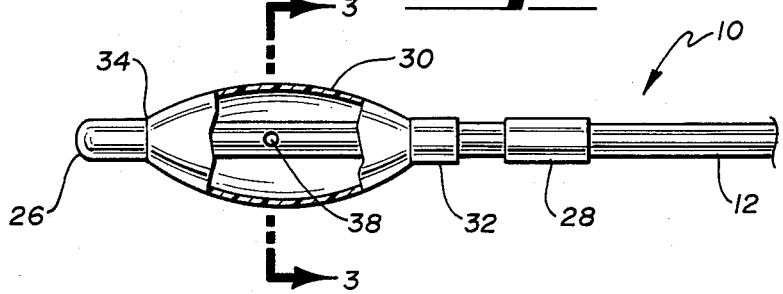
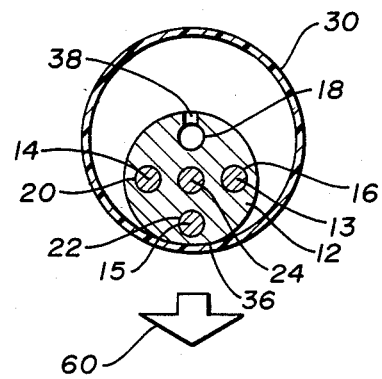
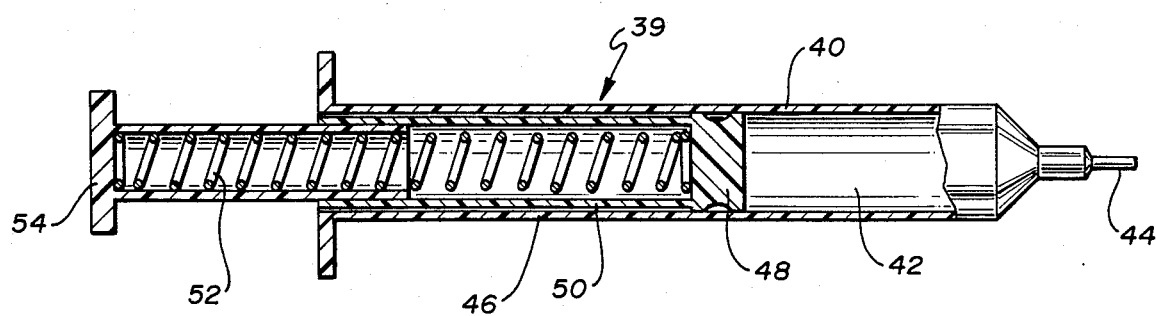

BALLOON LEAD AND INFLATOR

BACKGROUND OF THE INVENTION

The present invention relates to epidural leads with inflatable anchoring apparatus.

One type of lead commonly used for pain relief and other medical applications is advanced in to the epidural space next to the spine, so that the dura can be electrically stimulated. The location within the epidural space is critical, for a minor error in placement will result in ineffective stimulation. Placement is commonly made by inserting the lead and providing stimulation through an electrode. When relief is sensed in the desired area, the lead is left to permanently attach.

Many prior art devices provide varying means of anchoring a lead in its position within the epidural space. For example, the Medtronic PISCES-SIGMA ® lead has a generally S-shaped portion which bears against the walls of the epidural space to anchor the lead.

Another successful anchoring device is used in the Medtronic PISCES-SPIREL ™ lead which has small pliable plank-like tines at a distal end of the electrode for connecting by fibrosis to the walls of the epidural space. Additionally, the lead has a helically coiled section which bears out against the walls for anchoring and also for absorbing longitudinal pressures. This spring absorption of pressure further prevents lead dislodgment.

While these leads provide excellent anchoring apparatus, it is also desirable to urge the electrode toward the dura in order to maximize stimulation efficiency. The closer the electrode can be positioned in the dura, the lower the power requirements of the stimulating system. U.S. Pat. No. 4,285,347 to Hess, issued Aug. 25, 1981 discloses a lead for use in the epidural space which has a spring-like member at its distal end for urging electrode toward the dura. The flattening and extension of such a spring requires complicated insertion techniques.

Many implantable devices have used inflatable balloons for holding the device in a position in the body. U.S. Pat. No. 3,635,223 to Klieman discloses an embolectomy catheter which uses an inflatable portion for expanding angle protrusions to engage in embolus, so that the catheter can be withdrawn while gripping the emobolus. U.S. Pat. No. 3,937,225 to Schramm, issued Feb. 10, 1976 discloses a heart lead in which the electrode is anchored by the use of an expandable balloon. U.S. Pat. No. 4,331,133 to Robinson, issued Jan. 19, 1982 discloses an intra-aortic balloon with a flexible catheter.

U.S. Pat. No. 3,448,739 to Stark et al, issued June 10, 1969 shows a double lumen diagnostic balloon catheter in which an inner tube through the catheter allows fluid to be introduced in the balloon to inflate it.

U.S. Pat. No. 3,836,346 to Tower, issued Sept. 24, 1974, discloses another pacing catheter which employs a balloon for cushioning. A pacing lead with a balloon is also marketed by Siemens-Elema as Model 289 SM.

U.S. Pat. No. 4,198,963 to Barkalow et al, issued Apr. 22, 1980 discloses a heart defibrillator which is part of a cardiopulmonary resusitator. To aid in defibrillation, a catheter is inserted through the esophagus. The catheter has a balloon section which is positioned adjacent the heart. Because of the large relative size of this area, it is possible to have electrodes on the balloon. As the balloon is inflated, the esophagus is blocked to prevent food and gastric juices from escaping. The flexible metal strip electrode on the balloon is urged toward the heart. This patent discloses how a syringe may be used to inflate the balloon.

U.S. Pat. No. 3,326,207 to Egan, issued June 20, 1967, discloses a two-balloon system which is used for EKG testing of a fetus in the womb of a mother. One balloon is positioned adjacent the trunk of the fetus and the other adjacent its head. Multiple electrodes are positioned on the balloon. When the balloons are inflated one electrode from each set is likely to be in contact with the fetus. That one of the multiple electrodes is then chosen for electric sensing.

These many uses of balloons all show the common prior art technique of 360° inflation drawn on a catheter to anchor the catheter and to seal the area between the catheter and the body part. These prior art techniques do not allow the directional use of an inflatable balloon for urging an electrode transversely on a lead used in a narrow body cavity such as the epidural space.

SUMMARY OF THE INVENTION

A lead for use in a narrow body cavity, such as the epidural space or spinal canal, comprises an elongated lead body having a conductor mounted within the lead body, generally along the longitudinal axis of the lead. An electrode is mounted on the lead body and conductively connected to the conductor. This electrode may be any one of many common electrode configurations, such as a tip electrode, ring electrode, or a plate electrode on one side of the lead body.

A balloon is mounted on a lead for inflation and expansion generally in one direction, so that it expands less than 360° relative to the longitudinal axis. This expansion creates a net force in a direction transverse to the longitudinal axis for urging the electrode toward the area to be stimulated. Means are provided for inflating the balloon from a location distant from the electrode, such as prior art techniques of having a passage through the electrode open to the balloon for the introduction of fluid.

The inflatable means is preferably a balloon formed from an elastomeric cylinder. The cylinder is flipped over the lead. Each end of the cylinder is attached and sealed to the lead body. The cylinder is also sealed to the lead body along an area parallel to the longitudinal axis. This seals a portion of the balloon cylinder to the lead so that inflation results in new expansion perpendicular to the longitudinal axis in the direction of the seal.

The lead is inserted in the epidural space with the electrode positioned for contact with the dura. When it is properly positioned, the balloon is inflated to urge an electrode toward the dura to provide good contact.

An inflator for the balloon involves a syringe, for introducing the fluid in the manner of the prior art, which includes novel spring tension-absorbing means. The syringe has a fluid-holding body with a plunger for movement to eject fluid through a needle tip. A spring with preset tension is mounted within the plunger. An actuator element rides within the plunger against the tension of the spring. When fluid is to be introduced through the lead into the balloon, the actuator is depressed to push down the plunger, thereby ejecting fluid. When fluid pressure in the balloon reaches a predetermined level, the spring absorbs the pressure applied to the actuator and prevents further compression movement of the plunger. Therefore, the desired maximum pressure within the balloon is not exceeded.

BRIEF DESCRIPTION OF THE DRAWINGS

FIG. 1 is a side elevational view of a lead employing a balloon device constructed according to the present invention;

FIG. 2 is a top plan view of the lead of FIG. 1;

FIG. 3 is a cross-sectional view taken on line 3—3 of FIG. 2; and

FIG. 4 is a cross-sectional view of a syringe for inflating the balloon of FIG. 2, containing the pressure-absorbing device constructed according to the present invention.

DETAILED DESCRIPTION

A lead 10, constructed according to the present invention includes a lead body 12 which is, in this example, in the form of an elongated cylinder. Any of the types of prior art implantable leads may be used to practice the present invention. Lead 10 includes conductors 13, 14, and 15 which extend generally the entire length of lead 10. In the example illustrated, lead body 12 includes five lumens, 16, 18, 20, 22 and 24. In this example, conductors 13, 14 and 15 pass through lumens 16, 20 and 22 respectively. Lumen 24, the central lumen, is used for passing a stylet. A stylet is a metal wire used for stiffening the lead during insertion. Many other conductor configurations could be used, such as the common technique of including a helical coil conductor through lead body 12.

Mounted on lead body 10 are two electrodes 26 and 28. The electrodes 26 and 28 illustrated are merely representative of the many types of electrodes which can be used to practice the present invention. Electrode 26 is a tip electrode—which is conductively attached to one of conductors 13, 14 and 15 and mounted over the distal end of lead body 12. Electrode 28 is a ring electrode crimped over lead body 12 and conductively connected to one of conductors 13, 14 and 15. Although the illustrated example includes two electrodes and three conductors, any number or configuration of electrodes and conductors may be used.

A lead 10 constructed according to the present invention includes inflatable means, which in this case is a balloon 30 mounted on lead body 12. The balloon 30 illustrated is an elastomeric cylinder which is slid over lead body 12. Ends 32 and 34 of balloon 30 are attached to lead body 12 to form a fluid-tight seal around the lead body. In the example shown, lead 34 lies under tip electrode 26. Any common adhesive used in prior art balloon leads may may be used for attaching balloon 30.

An additional attachment between balloon 30 and lead body 12 is made at contact area 36, which is best shown in FIGS. 1 and 3. This is an area extending from end 32 to end 34 of balloon 30, generally along a longitudinal axis of lead 10. By sealing balloon 30 to lead body 12 along contact area 36, balloon 30 is free to expand away from lead body 12 only in those areas where it is not adhered to lead body 12. This results in an expansion of balloon 30 which is not coaxial with lead body 12. The expansion of balloon 12 is less than 360° around the longitudinal axis of the lead body 12.

One technique for applying balloon 30 to lead 20 involves applying a release agent on all areas of inflation of balloon 30, leaving contact area 36 and ends 32 and 34 to receive adhesive. The release agent will prevent fixation of balloon 30 and allow the appropriate asymmetric inflation.

Fluid is introduced to balloon 30 for inflation through inflation hole 38 which extends through lead body 12 to an internal passage through lead body 12, in this case, lumen 18. Fluid is introduced through lumen 18 and inflation hole 38 until balloon 30 has reached its desired expanded size. The fluid may be gas, such as air, or may be liquid, such as a saline solution. Any of the other prior art inflation techniques illustrated in balloon leads may be used for inflating a balloon constructed according to the present invention.

A syringe 39 for use in inflating balloon 30 is illustrated in FIG. 4. Syringe 39 includes a syringe body 40 which is provided with a fluid reservoir 42. Fluid is forced out of reservoir 42 through needle tip 44, which is in the end of syringe body 40 and open to reservoir 42.

A plunger 46 mounted within syringe body 40 includes a seal 48 and cylindrical body 50. As cylindrical body 46 urges seal 48 towards fluid reservoir 42, fluid is forced out of needle 44.

A spring 52 is mounted within cylindrical body 50. A plunger actuator 54 is mounted over an opposite end of spring 52. When plunger actuator 54 is urged by thumb pressure towards fluid reservoir 44, spring 52 is compressed and seal 48 is urged forward in fluid reservoir 42 to move fluid. Spring 52 is chosen with a preset tension so that when a desired fluid pressure within balloon 30 is reached, the back pressure against seal 48 prevents further movement of plunger 46. Additional pressure against plunger actuator 34 is absorbed by spring 52. This prevents over inflation and excessive pressure in balloon 30.

A lead 10 constructed according to the present invention is inserted in the epidural space, or other narrow body cavity, in the same manner as prior art stimulating leads. This is done, for example, by inserting a stylet through the lead. The lead is then inserted in the epidural space. The stylet is then retracted. Positioning of the lead to involve proper stimulation by electrodes is done in the same manner as the prior art. When the lead is positioned, balloon 30 is inflated through means such as syringe 39. The method of attaching syringe 30 to lumen 18 of lead body 12 may employ any of the common prior art techniques.

Once balloon 30 is inflated, a lead is firmly anchored in the spine and electrodes 26 and 28 are urged in a direction indicated by arrows 56 and 58. This is because balloon 30 expands other than coaxially with lead body 12. This results in a net force in a direction perpendicular to the longitudinal axis of lead body 12, such as illustrated by arrow 60 in FIG. 3. Lead 12 is arranged so that the dura or other area to be stimulated lies in a direction away from lead 12 such as that of arrow 60. When balloon 30 is inflated, the net force of inflation against the inner walls of the epidural space or spinal canal urges the electrodes 26 and 28 toward the area to be stimulated. This provides not only sound fixation, but maximum stimulating ability of the electrodes. Once anchored in place, fibrosis around balloon 30 will firmly anchor lead 12. After a period of fibrosis, balloon 30 need no longer be inflated.

Although the present invention is illustrated by a particular embodiment, it will easily be seen by those skilled in the art that other embodiments may be used to practice the invention, including other electrodes, lumen configurations, or balloon apparatus.

What is claimed is:

1. A lead for insertion in the epidural space comprising:
    an elongated lead body having a longitudinal axis;
    a conductor mounted longitudinally within the leady body;
    an electrode mounted on the lead body and conductively connected to the conductor;
    inflatable means mounted on the lead body for expansion away from the lead body in a first direction so that contact with walls of the epidural space imparts a net force in a second direction transverse to the longitudinal axis, thereby urging the electrode in the second direction; and
    means for passing fluid through the lead body for inflating the inflatable means.

2. The lead of claim 1 wherein the inflatable means is a balloon of elastomeric material.

3. The lead of claim 2 wherein the balloon is formed generally as a cylinder, the cylinder being slipped over the lead body and attached to the lead body at each end of the cylinder, the cylinder being further attached to the lead body along a contact area parallel to the longitudinal axis of the lead body from one end of the cylinder to the other end of the cylinder.

4. The lead of claim 1 wherein the means for passing fluid is a lumen through the lead body open to the inflatable means.

5. An epidural lead for spinal cord stimulation comprising:
    a lead body sized to fit in an epidural space having a longitudinal axis;
    a conductor mounted longitudinally within the lead body;
    electrode means mounted on the lead body and conductively connected to the conductor for stimulating dura;
    inflatable means mounted on the lead body for expanding in a first direction to a size contacting walls of the epidural space, for urging the electrode in a second direction toward the dura, and for preventing longitudinal movement of the lead body; and
    means for passing fluid through the lead body for inflating the inflatable means.

6. The lead of claim 5 wherein the inflatable means is a balloon of elastomeric material.

7. The lead of claim 6 wherein the balloon is formed generally as a cylinder, the cylinder being slipped over the lead body and attached to the lead body at each end of the cylinder, the cylinder being further attached to the lead body along a contact area parallel to the longitudinal axis of the lead body from one end of the cylinder to the other end of the cylinder.

8. The lead of claim 5 wherein the means for passing fluid is a lumen through the lead body open to the inflatable means.

* * * * *